US00PP28469P3

(12) United States Plant Patent
Bradford et al.

(10) Patent No.: US PP28,469 P3
(45) Date of Patent: Oct. 3, 2017

(54) PLUM TREE NAMED 'PLUMSWEET XVIII'

(50) Latin Name: *Prunus salicina*
Varietal Denomination: Plumsweet XVIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 37 days.

(21) Appl. No.: 14/757,264

(22) Filed: Dec. 11, 2015

(65) Prior Publication Data

US 2017/0172027 P1 Jun. 15, 2017

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP23,686 P2 6/2013 Bradford

*Primary Examiner* — Keith Robinson

(57) ABSTRACT

The present invention relates to a plum tree and more particularly to a new and distinct variety broadly characterized by a large size, vigorous, hardy, and productive tree. Being self-unfruitful, the present variety requires cross pollination from an apricot, interspecific, or plum that blooms during the mid season, such as 'September Yummy' plum (U.S. Plant Pat. No. 14,220). The present variety's abundance of blossoms and moderate pollen production entices strong bee activity to facilitate pollination. The fruit matures under the ecological conditions described during late June, with first picking on Jun. 29, 2015, and will hang on the tree for at least fifteen more days. The fruit is uniformly large in size, yellow with heavy red dappling skin color, clingstone in type, heart shaped, full red in flesh color, very firm and crisp in texture, and very good in flavor.

1 Drawing Sheet

Botanical classification: *Prunus salicina.*
Varietal denomination: 'PLUMSWEET XVIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'Plumsweet XVIII'.

During a typical blooming season we isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2003 one such house containing an unpatented purple plum, code named '42P1156', was crossed by us in this manner. To pollinate this purple plum, we selected bouquets from several plum trees without keeping specific written details. Upon reaching maturity the fruit from this plum tree was harvested, and the seeds were removed, cracked, stratified and germinated as a group with the label "H12". They were grown as seedlings on their own root in our greenhouse and upon reaching dormancy transplanted to a cultivated area of our experimental orchard located near Le Grand, Calif. in Merced County (San Joaquin Valley). During the summer of 2007 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was true to type.

The present variety is similar to its seed parent, '42P1156' (unpatented) plum tree, by being self-unfruitful and producing fruit that is firm, that is juicy, and that matures in the mid season, but is quite distinguished therefrom by producing fruit that is yellow with dark red dappling instead of solid red to purple in skin color, red instead of yellow in flesh color, sweeter, and oblong to heart shaped instead of globose.

The present variety is most similar to 'Plumsweet XIV' (U.S. Plant Pat. No. 23,686) interspecific tree by blooming in the mid season, by being self-unfruitful, and by producing fruit that is clingstone in type, that is sweet, that is firm, that is juicy, that is very good in flavor, and that ripens in the mid season, but is distinguished therefrom by having a larger tree and by producing fruit that is oblong to heart shaped instead of globose, that has much stronger red dappling on the skin, and that is much larger in size.

SUMMARY OF VARIETY

The present plum variety is characterized by a large size, vigorous, hardy, and productive tree. Being self-unfruitful, the present variety requires cross pollination from an apricot, interspecific, or plum that blooms during the mid season, such as 'September Yummy' plum (U.S. Plant Pat. No. 14,220). The present variety's abundance of blossoms and moderate pollen production entices strong bee activity to facilitate pollination. The fruit matures under the ecological conditions described during late June, with first picking on Jun. 29, 2015, and will hang on the tree for at least fifteen more days. The fruit is uniformly large in size, yellow with heavy red dappling skin color, clingstone in type, heart shaped, full red in flesh color, very firm and crisp in texture, and very good in flavor.

DRAWING

The accompanying photograph consists of four whole fruits positioned to display the characteristics of the skin color and form, one divided fruit to reveal the flesh and stone, one tip shoot, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jul. 9, 2015, on the original tree during its twelfth growing season. The flower and bud descriptions were developed during the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: '42P1156' plum (unpatented).
Pollen parent: Unknown.

TREE

Size: Large, reaching and maintaining a height of 12' [3.66 m.] and a spread of 9' [2.74 m.] after twelve growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to a vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming plum or interspecific, such as 'September Yummy' plum tree (U.S. Plant Pat. No. 14,220).

Bearing: Regular bearer, weather dependent, with no crop failures observed as of yet.

Trunk:

*Size.*—Stocky, reaching a maximum diameter of 6" [152 mm.] after the twelfth growing season.

*Texture.*—Medium roughness.

*Bark color.*—A Dark grayish brown [62. d.gy.Br] and Dark brown [59. d.Br] variegation with Light grayish brown [60. l.gy.Br] crevices present.

*Lenticels.*—Approximate Number Per Square Inch: 5. Color: Moderate orange [53. m.O]. Average Size: ¼" [6.4 mm.] in length. The width is typically one fourth as much as the length. Shape: Eye-shaped.

Branches:

*Size.*—Medium, diameter of limb is 3½" [89 mm.] measured 12" above the crotch, 1⅞" [48 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. 2nd Year Wood: A Dark grayish brown [62. d.gy.Br] and Light yellowish brown [76. l.yBr] variegation.

*Lenticels.*—Number Per Square Inch: About 25 on second year wood. Color: Light orange yellow [70. l.OY]. Average Size: Small, 1/64" [0.4 mm.] in length. The width is typically one fourth as much as the length. Shape: Eye-shaped.

Leaves:

*Size.*—Medium. Average Length: 4⅛" [104.8 mm.]. Average Width: 1 9/16" [39.7 mm.].

*Arrangement.*—Alternate.

*Thickness.*—Medium.

*Form.*—Elliptical.

*Apex.*—Acuminate.

*Base.*—Acute with an average angle of sixty-five degrees.

*Surface.*—Smooth on both sides.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 11/16" [17.5 mm.]. Average Thickness: 1/16" [1.6 mm.]. Color: Light yellow green [119. l.YG].

*Stipules.*—Number: Typically 2 per leaf. Average Length: 5/16" [7.9 mm.]. Color: Brilliant yellow green [116. brill.YG] becoming Light grayish reddish brown [45. l.gy.rBr] with age.

*Glands.*—Number: Mostly 2 per leaf. Position: Mostly alternate, positioned near the intersection of the petiole and the base of blade. Form: Globose. Size: Medium, 1/48" [0.5 mm.] in diameter. Color: Brilliant yellow green [116. brill.YG] becoming Grayish brown [61. gy.Br] in the center with age. Leaf buds: Pointed.

Flower buds:

*Hardiness.*—Hardy, with respect to central California blooming season.

*Diameter.*—Typically 3/16" [4.8 mm.] 1 week before bloom.
*Length.*—Typically 3/8" [9.5 mm.] 1 week before bloom.
*Form.*—Not appressed.
*Surface.*—Slightly pubescent.
*Tip color.*—White [263. White].

Flowers: Perfect, complete, perigynous, usually a single pistil, typically thirty or more stamens, five sepals and petal locations alternately positioned.
*Average flower diameter.*—1 1/8" [28.6 mm.].
*Average flower depth.*—3/8" [9.5 mm.] when fully open.
*Average pedicel length.*—3/8" [9.5 mm.].
*Number of petals.*—Five, no double blossoms observed.
*Petal shape.*—Oval to circular.
*Petal margin.*—Entire, somewhat wavy.
*Average petal diameter.*—1/2" [12.7 mm.].
*Average petal length.*—9/16" [14.3 mm.].
*Petal apex.*—Rounded.
*Petal base.*—Obtuse.
*Petal color.*—White [263. White] on both sides.
*Anther color.*—Brilliant yellow [83. brill.Y].
*Pollen production.*—Moderate.
*Pollen color.*—Strong yellow [84. s.Y].
*Stigma color.*—Light greenish yellow [101. l.gY].
*Stigma position.*—Located slightly below the nearby anther height.
*Sepal color.*—Brilliant yellow green [116. brill.YG] with Light grayish red [18. l.gy.R] areas toward the apex on the outer surface. Light yellow green [119. l.YG] on the inner surface.
*Sepal length.*—3/16" [4.8 mm.].
*Sepal width.*—5/32" [4.0 mm.].
*Sepal apex.*—Rounded to elliptical to match the width and length.
*Sepal margin.*—Fairly smooth to the naked eye, slightly serrate when magnified.
*Average pistil length.*—1/2" [12.7 mm.], some blanks observed.
*Average stamen length.*—9/16" [14.3 mm.].
*Ovary.*—Smooth.
*Fragrance.*—Moderate.
*Blooming period.*—Medium compared to other varieties, two days before 'Santa Rosa' plum (unpatented).
*Onset of bloom.*—One percent on Feb. 16, 2015.
*Date of full bloom.*—Feb. 27, 2015.
*Duration of bloom.*—One to two weeks, dependent on ambient temperature.
*Bloom density.*—Very heavy, clustered.
*Number per cluster.*—2 to 12, average 5.

FRUIT

Maturity when described: Firm ripe, Jul. 9, 2015.
Date of first picking: Jun. 29, 2015.
Date of last picking: Jul. 15, 2015.
Size: Uniform, large.
*Average diameter axially.*—2 7/8" [73 mm.].
*Average diameter across cheek plane.*—2 9/16" [65.1 mm.].
*Average diameter across suture plane.*—2 1/2" [63.5 mm.].
*Typical weight.*—6.2 ounces [176 grams].
Form: Uniform, oblong and heart shaped.
*Longitudinal section form.*—Oval.
*Transverse section through diameter.*—Round.
Suture: A sharp crevice located in a shallow trough extending from the base to the apex.
Ventral surface: Rounded, slightly lipped on both sides.
Lips: Equal.
Cavity: Flaring, rounded, suture showing on one sides.
*Depth.*—9/16" [14.3 mm.].
*Breadth.*—1 1/8" [28.6 mm.].
Base: Truncate, strongly cordate when viewed parallel to the suture.
Apex: Rounded to mammiform.
Pistil point: An inconspicuous Light yellowish brown [76. l.yBr] dot located at the end of the suture.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Slight.
*Tendency to crack.*—None observed.
*Color.*—Dark red [15. d.R] mottled over a Moderate yellow [87. m.Y] background with heavy Pale greenish yellow [104. p.gY] freckling throughout.
*Lenticels.*—Number Per Square Inch: About 140 toward the apex. Average diameter: 1/48" [0.5 mm].
*Bloom.*—Moderate.
Flesh:
*Color.*—Very deep red [14. v.deep R] toward the skin, Vivid red [11. v.R] toward the stone.
*Surface of pit cavity.*—Covered with Moderate yellowish pink [29. m.yPk] broken fibers when twisted from stone.
*Amygdalin.*—Moderate.
*Juice.*—Abundant, rich.
*Texture.*—Firm, crisp, can remain on the tree for more than fifteen days.
*Fibers.*—Abundant, tender.
*Ripens.*—Fairly even.
*Flavor.*—A nice blend of acid and sugar, typically 18 brix.
*Aroma.*—Slight.
*Eating quality.*—Very good.

STONE

Type: Clingstone.
Form: Oval.
Hilum: Narrow, oval.
Base: Rounded.
Apex: Acute, with a sharp 1/16" [1.6 mm.] tip.
Sides: Equal.
Surface: Rounded.
External color of stone: Moderate orange yellow [71. m.OY].
Pit wall color when cracked: Light yellowish brown [76. l.yBr].
Cavity surface color: Strong yellowish brown [74. s.yBr].
Average pit wall thickness: 1/8" [3.2 mm.].
Average length: 1" [25.4 mm.].
Average width: 5/8" [15.9 mm.].

Average breadth: ⅜" [9.5 mm.].
Tendency to split: None observed.
Kernel:

*Form.*—Oval.
*Skin color.*—Strong yellowish brown [74. s.yBr].
*Pellicle color.*—Dark yellowish brown [78. d.yBr].
*Vein color.*—Deep yellowish brown [75. deep yBr].
*Taste.*—Somewhat bitter.
*Viable.*—Yes.
*Average length.*—⅝" [15.9 mm.].
*Average width.*—⅜" [9.5 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Plumsweet XIV' (U.S. Plant Pat. No. 23,686) interspecific tree by blooming in the mid season, by being self-unfruitful, and by producing fruit that is clingstone in type, that is sweet, that is firm, that is juicy, that is very good in flavor, and that ripens in the mid season, but is distinguished therefrom by having a larger tree and by producing fruit that is oblong to heart shaped instead of globose, that has much stronger red dappling on the skin, and that is much larger in size.

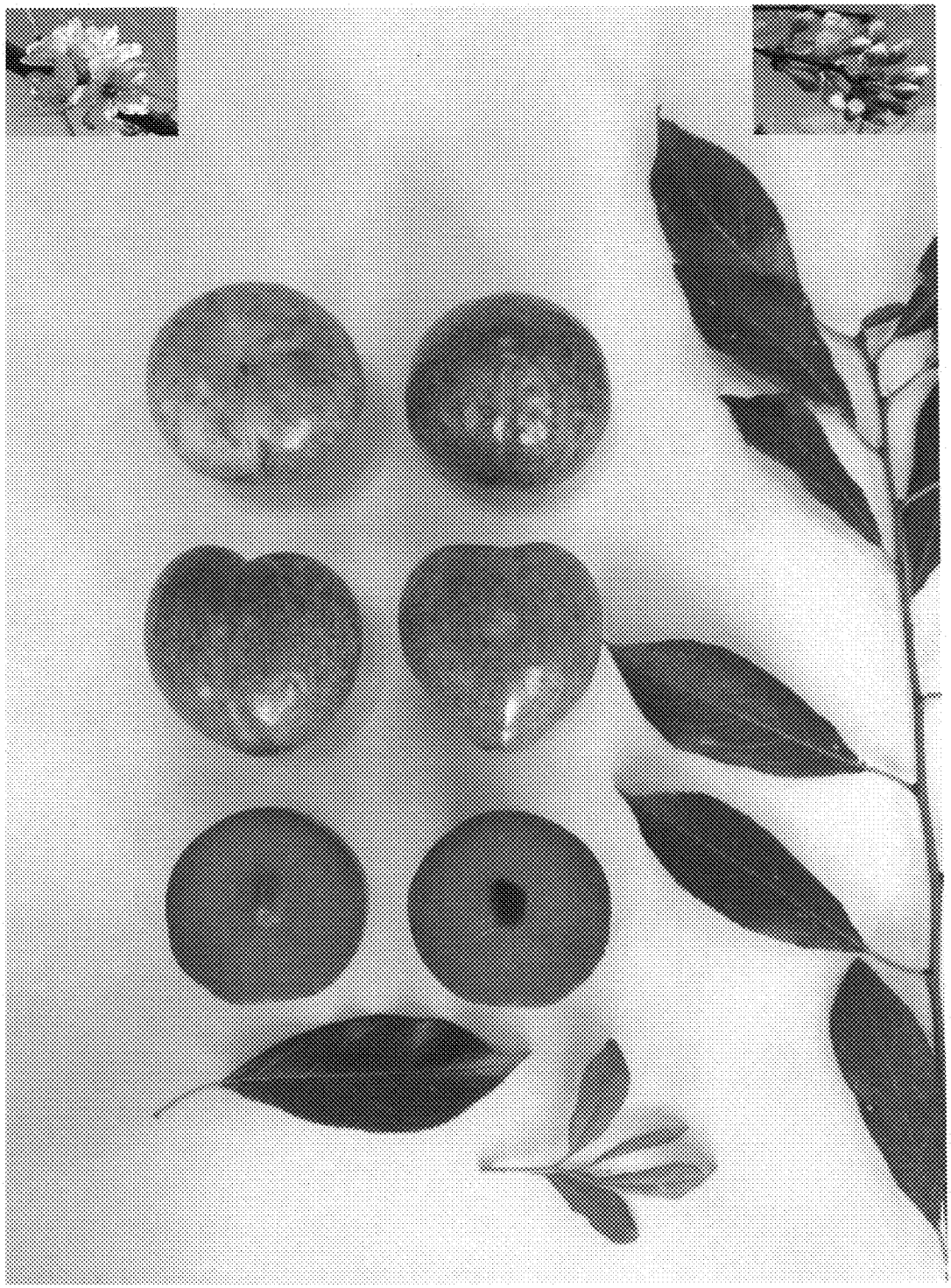

* * * * *